United States Patent

Von Weissenfluh et al.

Patent Number: 6,019,603
Date of Patent: Feb. 1, 2000

[54] DENTAL INSTRUMENT COMPRISING AN ABRASIVE DISK AND A SPINDLE, AND PROCESS FOR MANUFACTURING AN ABRASIVE DISK

[75] Inventors: Hans Von Weissenfluh, Magadino; Beat Kilcher, Bosco Luganese; Beat A. Von Weissenfluh, Gentilino, all of Switzerland

[73] Assignee: Hawe Neos Dental Dr. H. v. Weissenfluh AG, Bioggio, Switzerland

[21] Appl. No.: 09/252,493

[22] Filed: Feb. 18, 1999

[30] Foreign Application Priority Data

Feb. 18, 1998 [EP] European Pat. Off. .............. 98810128

[51] Int. Cl.[7] ....................................................... A61C 3/06
[52] U.S. Cl. ............................................. 433/166; 433/134
[58] Field of Search ..................................... 433/134, 166, 433/142, 125, 127; 451/504, 507, 514, 526

[56] References Cited

U.S. PATENT DOCUMENTS

| | | | |
|---|---|---|---|
| 1,314,125 | 8/1919 | Burlew ..................................... | 433/134 |
| 2,842,844 | 7/1958 | Seal ......................................... | 433/166 |
| 3,270,468 | 9/1966 | Block et al. ............................. | 451/514 |
| 3,561,938 | 2/1971 | Block et al. ............................. | 451/514 |
| 3,858,368 | 1/1975 | Cocherell et al. ...................... | 451/490 |
| 4,624,876 | 11/1986 | Nevin ........................................ | 428/65 |
| 4,889,489 | 12/1989 | Von Weissenfluh ..................... | 433/134 |
| 4,988,294 | 1/1991 | DuBe et al. ............................. | 433/134 |
| 5,842,250 | 12/1998 | Zhadanov ................................. | 451/359 |

FOREIGN PATENT DOCUMENTS

WO 88/00029  1/1988  WIPO.

*Primary Examiner*—Nicholas D. Lucchesi
*Attorney, Agent, or Firm*—Young & Thompson

[57] ABSTRACT

The dental device comprises an abrasive disk having a hub made of synthetic material and a spindle with a collet, the opening of the hub having an inner bead and the collet a rotation lock and an axial lock for receiving said bead in the hub opening, the greatest diameter of the spindle with its rotation lock being greater than the diameter of the hub opening with its bead. This construction allows, on one hand, an easier mounting of the abrasive disk on the spindle, and, on the other hand, a high torque transmission.

10 Claims, 4 Drawing Sheets

DENTAL INSTRUMENT COMPRISING AN ABRASIVE DISK AND A SPINDLE, AND PROCESS FOR MANUFACTURING AN ABRASIVE DISK

BACKGROUND OF THE INVENTION

The present invention refers a dental device comprising an abrasive disk having a hub and a spindle with a collet, the opening of the hub and the cross section of the collet being complementary to each other in order to get a removable fastening of the abrasive disk on the spindle.

A plurality of dental instruments are already known which are used for the treatment of dental fillings, this work being typically carried out in several steps, beginning with rough-working until fine polishing. In these operations, it is necessary to use different abrasive disks, and different devices are at hand to carry out the exchange of the tool in a simple and rapid manner. Systems having non-positive or positive connection have been proven as useful.

U.S. Pat. No. 4,889,489 discloses a dental device in which the spindle has a square end, and the hub of the abrasive disk has a corresponding four-edged opening in order to achieve a positive coupling. The device allows to transmit a higher torque but has the drawback that the abrasive disk, when it is to be connected with the spindle, must always be brought into a correct position with respect to the spindle.

U.S. Pat. No. 4,988,294 discloses another dental device in which the free end of the spindle is rotationally symmetrically shaped and provided with slots in order to receive a hard hub being also rotationally symmetrically shaped. The slotted end of the spindle is spread out by the action of the centrifugal force generated by the rotation of the spindle, and the disk is retained on the spindle. However, the torque which can be transmitted is rather small whereas the disk can be inserted on the end of the spindle in any position whatsoever.

SUMMARY OF THE INVENTION

Starting from the above discussed prior art, there is a first and major object of the invention to provide a dental device or instrument of the above described kind which combines the advantages of the two approaches, namely of the non-positive and the positive coupling possibilities, and which avoids the drawbacks of the known devices such as the requirement of a correct positioning of the disk with respect to the spindle and the rather low torque transmission.

This object is attained with the device of this invention wherein the opening of the hub is provided with an inner bead and the collet is equipped with a rotation lock and an axial lock for receiving said bead in the opening of the hub, the greatest diameter of the spindle with its rotation lock being greater than the diameter of the hub opening with its bead.

Another object of the present invention is to improve and to render easier the manufacture of an abrasive disk. This object is achieved by the process of this invention, wherein the hub, made of a synthetic material, and the disk having a central opening, are manufactured separately and are then combined with each other, the hub having a supporting surface and, distant from this surface, a fastening surface, the hub is then introduced through the opening of the disk until the disk contacts the supporting surface, and the fastening surface is then thermally applied to the disk and mechanically anchored thereto.

The invention will now be explained in more detail with the aid of drawings of embodiments.

DETAILED DESCRIPTION OF THE INVENTION

The abrasive disk 1 has a hub 2 that is provided with a rotationally symmetrical hub opening 3. It can be seen in FIG. 2 that the hub opening 3 has a central peripheral bead 4 in such a manner that the diameter of the bead is smaller than that of the remaining opening 3. The hub is formed of a resilient and elastic synthetic material and has a mirror symmetry with respect to the plane in which the disk is situated.

In the present embodiment, the abrasive disk is not flat as in the prior art cited above but cambered. The abrasive coating may be applied to the concave or to the convex surface, or on both, and may comprise abrasive particles having different diameters.

Figure 1:
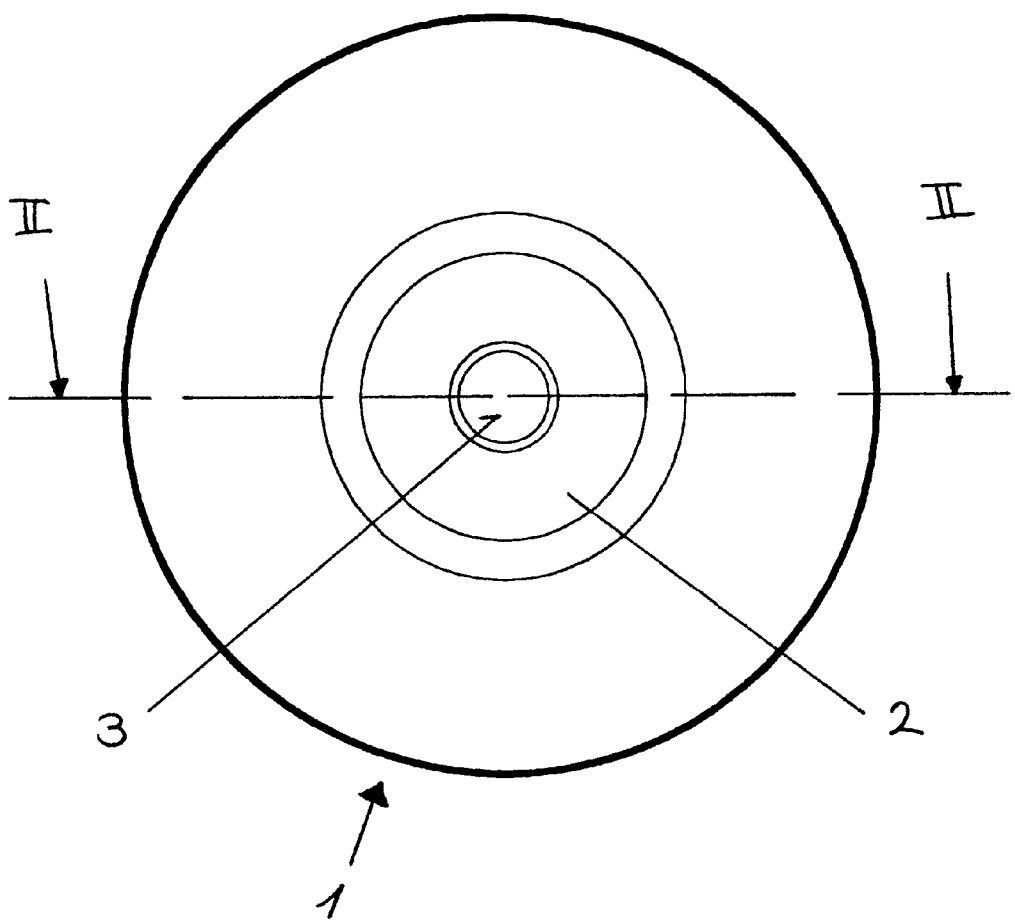
FIG. 1 shows a top view of an abrasive disk according to the invention.
Figure 2:
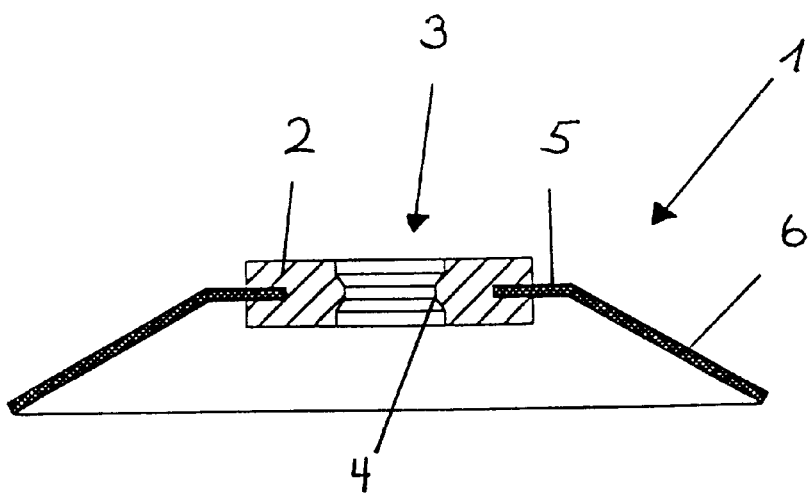
FIG. 2 is a section according to line II—II in FIG. 1.

In the embodiment of FIG. 2, the camber of the abrasive disk is not continuous; an essentially flat central portion 5 is followed by a bent-off portion 6 so that the disk has a lamp-shade like shape. However, it is also possible to have a continuous camber. The camber radius may be, for both kinds of disks, comprised between about 8 and about 20 mm, preferably around about 14 mm. The disks may have a thickness of, for example, from 0.05 to 0.5 mm and a diameter of from about 8 to about 20 mm. The hub opening may have a diameter of about 2.25 mm whereas the hub thickness may be comprised between about 1 and 1.5 mm. The material of the abrasive disk body may be a relatively stiff sheet of a polyester; in this way, the abrasive disk can be deflected so that the concave surface becomes convex and vice versa.

Figure 3:
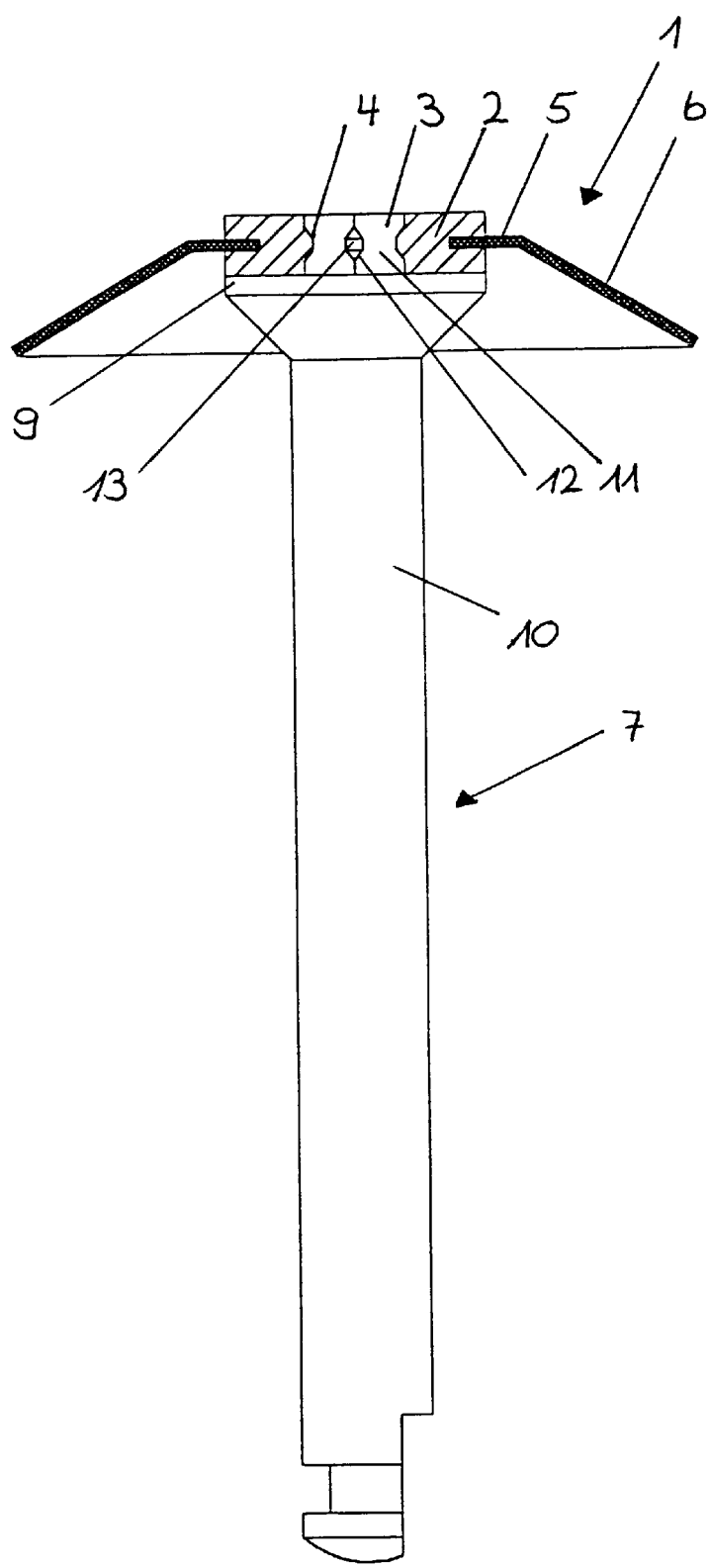
FIG. 3 is a cross-sectional view of the abrasive disk of FIG. 1, mounted on a spindle.
Figure 4:
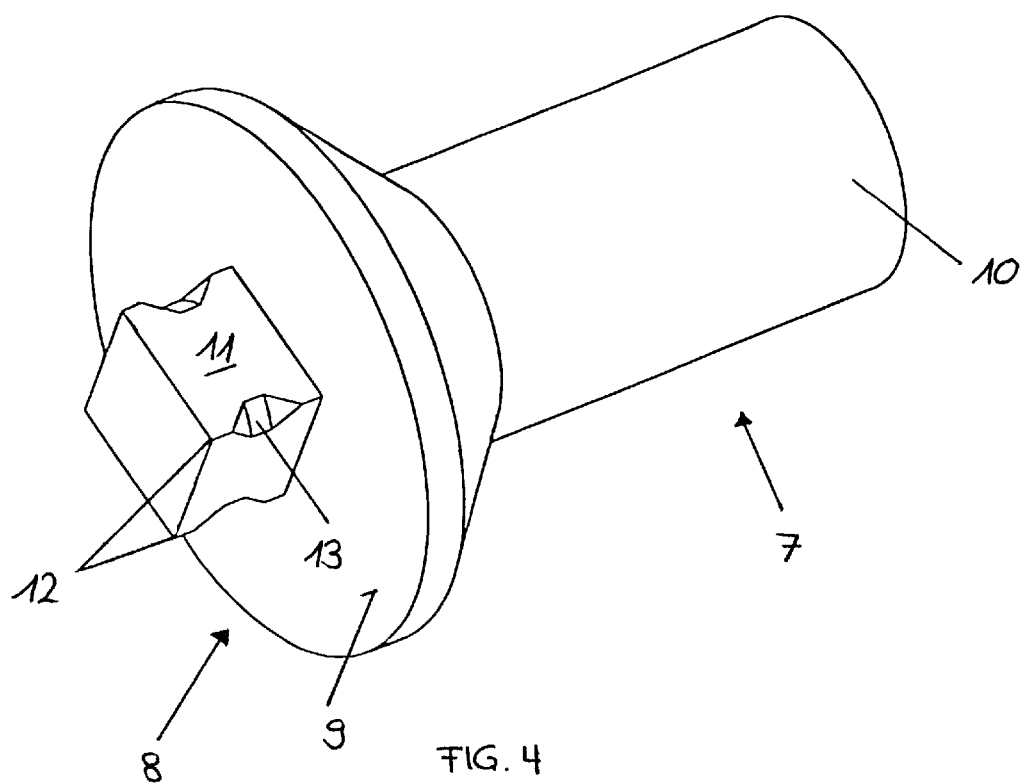
FIG. 4 is a perspective view of a first embodiment of a spindle.

FIG. 3 shows a spindle 7 with an abrasive disk mounted thereon. The receiving end of the spindle is provided with a collet head 8 which is preferably made of a relatively hard synthetics or of a metal. The collet head 8 has a disk-shaped receiving surface 9 whose diameter is greater than that of the spindle shaft 10. The surface of the collet 11 is provided with means 12 serving as a rotation lock in order to ascertain a good torque transmission. In the embodiment of FIG. 4, the collet 8 has a rectangular or square cross section, the edges of the rectangle serving as a rotation lock 12.

In order to receive the bead 4 of the hub opening, the collet 11 comprises recesses 13 that serve as an axial lock, and are disposed in this example on the rotation lock 12, the bead 4 of the hub opening and the recesses 13 being coordinated in such a manner that the bead snaps into the recesses when the disk is mounted on the spindle and secures the disk thereto in an axial direction. Furthermore, the greatest diameter of the rotation lock of the collet is greater than the greatest diameter of the bore 3 of the hub 2 so that the corners and the edges or, respectively, the rotation lock 12 will penetrate into the opening of the hub in using its elasticity and resiliency and secure the disk against rotation with respect to the spindle. Furthermore, the length of the collet is selected in such a manner that it does not protrude, when the hub is received, from the latter.

Figure 5:
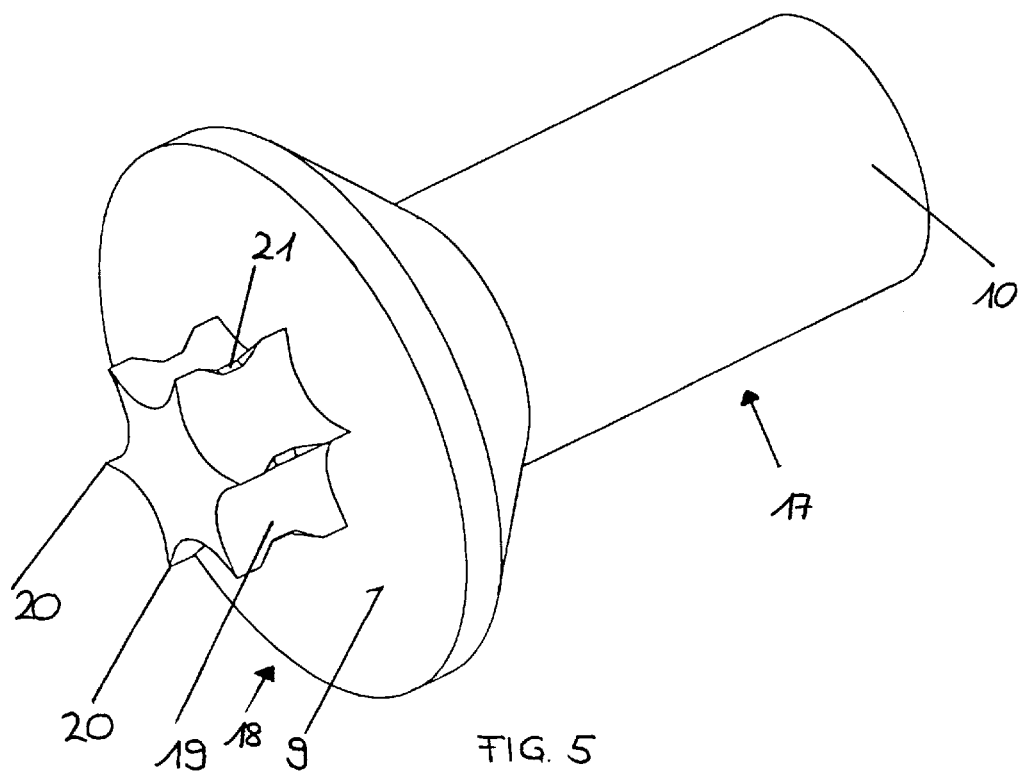
FIG. 5 is a perspective view of a second embodiment of a spindle.

However, it is also possible to use a triangular or a polygonal rotation lock instead of a square device, or even other rotation locking means. In the embodiment shown in FIG. 5, the spindle head 18 can be seen whose collet 19 has, for example, a star-shaped section, the edges 20 serving as a rotation lock and having recesses 21 as an axial lock.

The disk may now be mounted on the spindle independently on its orientation, whereas simultaneously the connection thus obtained, which is a non-positive connection and a positive one as well, ascertains a safe transmission of the torque. The mirror symmetry of the hub allows the mounting on of the disk in either direction.

Due to the construction of the abrasive disk according to the invention, it is further possible to simplify its manufacture. The disk as well as the hub of synthetic material can be manufactured separately and then combined with each other. This is in contrast with the manufacturing techniques of the disk according to U.S. Pat. No. 4,889,489 where the hub is injected on the disk.

Figure 6:
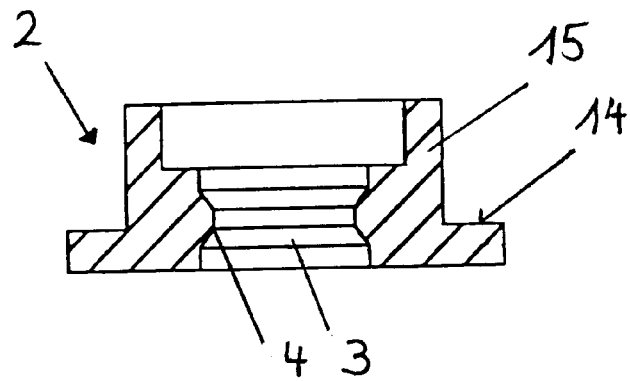
FIGS. 6 to 8 are cross-sectional views of three process steps during the manufacture of the abrasive disk according to the invention.

The prefabricated hub according to FIG. 6 comprises a supporting surface 14, the hub opening 3 and the bead 4 in the hub opening, and a clamping portion 15 having a distance from the supporting surface which corresponds to about the thickness of the disk. The disk has been punched out of a ribbon coated with abrasive materials and provided with an opening 16 for the hub.

Figure 7:
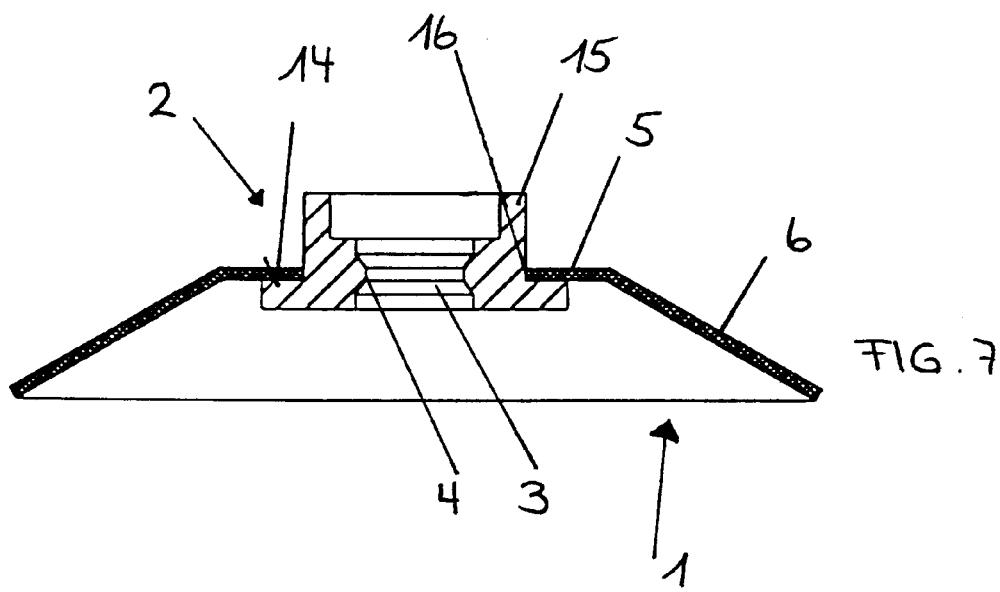
Figure 8:
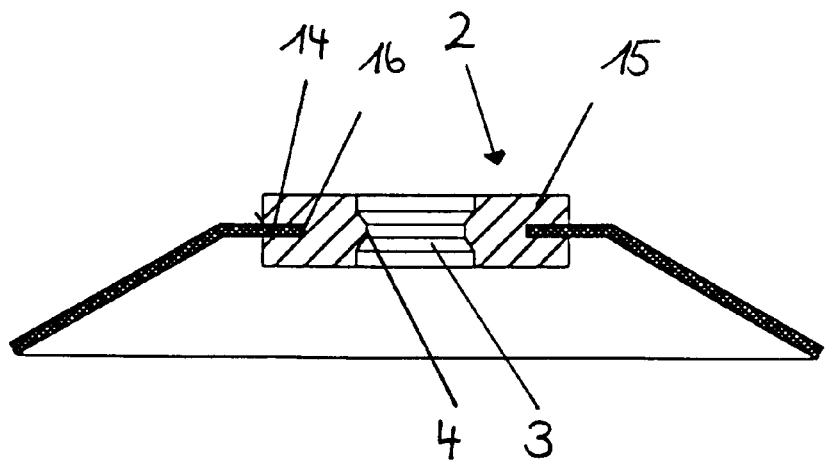

For assembling, see FIGS. 7 and 8, the prefabricated hub is inserted from one side of the disk into its opening 16 until coming into contact with the supporting surface 14. The clamping portion 15 of the hub is thermally shaped and brought upon the disk where it is mechanically anchored. All working steps can be carried out mechanically and in a fully automatic manner with relatively small costs. This allows the use of conventional and simple tools and machines.

In the embodiments described above, cambered disks are described. However, it is obvious that the connection of the disk to the spindle and the method of manufacturing the disks as well can be applied to flat disks too.

We claim:

1. A dental device comprising an abrasive disk having a hub and a spindle with a collet, an opening of the hub and a cross section of the collet being arranged and constructed to provide a removable fastening of the abrasive disk on the spindle, wherein the opening of the hub is provided with an inner bead and the collet is equipped with a rotation lock and an axial lock for receiving said bead in the opening of the hub, a greatest exterior diameter of the rotation lock being greater than an interior diameter of the hub opening.

2. A dental device according to claim 1, wherein the rotation lock comprises edges of the collet extending in an axial direction of the spindle.

3. A dental device according to claim 1, wherein the cross section of the collet is a polygon, the axial lock comprising recesses which are disposed in the polygon edges.

4. A dental device according to claim 1, wherein the hub is made of resilient and elastic synthetic material, and the spindle is made of a harder synthetic material or of metal.

5. A dental device according to claim 1, wherein said disk is flat or is cambered.

6. A dental device according to claim 5, wherein the disk has one of a continuous camber and a cambered periphery with a flat central portion.

7. A dental device according to claim 6, wherein the disk thickness and material are selected so that the camber is reversible.

8. A dental device according to claim 5, wherein the disk thickness and material are selected so that the camber is reversible.

9. Process for the manufacture of an abrasive disk having a hub with an opening, wherein the hub, made of a synthetic material, and the disk having a central opening, are manufactured separately and are then combined with each other, the hub having a supporting surface and, distant from this surface, a fastening surface, the hub is being introduced through the opening of the disk until the disk contacts the supporting surface, and the fastening surface is then bent over onto the disk and mechanically anchored thereto.

10. A dental de vice comprising:

an abrasive disk having a hub, said hub having a central opening with a radially inwardly extended bead surrounding on an interior surface of the opening; and a spindle having a collet at one end, said collet comprising a material that is harder than a material of said hub, said collet further comprising a polygon with edges that extend in an axial direction of the spindle and whose maximum exterior diameter is greater than an interior diameter of the opening to rotationally lock said hub on said collet and with recesses in the edges that receive said bead to axially lock said hub on said collet, when said disk is mounted on said spindle.

* * * * *